United States Patent
Popescu et al.

(10) Patent No.: US 7,636,415 B2
(45) Date of Patent: Dec. 22, 2009

(54) METHOD FOR PRODUCING TOMOGRAPHIC PICTURES WITH THE AID OF AN X-RAY COMPUTED TOMOGRAPHY SYSTEM WITH SCATTERED RADIATION CORRECTION

(75) Inventors: Stefan Popescu, Erlangen (DE);
Herbert Bruder, Höchstadt (DE);
Christoph Suess, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/071,108

(22) Filed: Feb. 15, 2008

(65) Prior Publication Data
US 2008/0198965 A1     Aug. 21, 2008

(30) Foreign Application Priority Data
Feb. 19, 2007   (DE) .................. 10 2007 008 118

(51) Int. Cl.
*G01N 23/00*    (2006.01)
(52) U.S. Cl. .............................................. 378/7; 378/9
(58) Field of Classification Search ............. 378/4, 378/7, 8, 9, 15, 16, 70, 86, 87, 114–116
See application file for complete search history.

(56) References Cited

U.S. PATENT DOCUMENTS

| | | | |
|---|---|---|---|
| 6,198,790 B1 | 3/2001 | Pflaum | |
| 6,421,412 B1 | 7/2002 | Hsieh | |
| 6,876,719 B2 | 4/2005 | Ozaki | |
| 7,016,455 B2 | 3/2006 | Bruder et al. | |
| 2004/0228442 A1 | 11/2004 | Sakaguchi | |
| 2007/0086561 A1 | 4/2007 | Bruder et al. | |

FOREIGN PATENT DOCUMENTS

| | | |
|---|---|---|
| DE | 198 02 405 B4 | 1/1998 |
| DE | 103 02 565 A1 | 1/2003 |
| EP | 1405598 A1 | 4/2004 |

OTHER PUBLICATIONS

2002E18315DE, filed May 6, 2003, Bruder, Herbert, German Office Action, Oct. 8, 2007.

*Primary Examiner*—Jurie Yun
(74) *Attorney, Agent, or Firm*—Harness, Dickey & Pierce, P.L.C.

(57) ABSTRACT

A method and an X-ray CT system are disclosed for producing tomographic pictures with the aid of an X-ray CT system including at least two X-ray sources arranged on a gantry with an angular offset to scan an examination object. In at least one embodiment of the method, in order to determine the scattered radiation distribution, pre-scanning is carried out in which the X-ray sources rotate about the examination object and the dose rate is modulated as a function of the rotation angle, no radiation dose is output over the majority of the revolution, at specific pre-scan angles a dose rate is produced briefly and individually in each case by the X-ray sources of the focus/detector systems, and the received scattered radiation is measured simultaneously by the detectors of the at least one other focus/detector system.

25 Claims, 9 Drawing Sheets

FIG 5
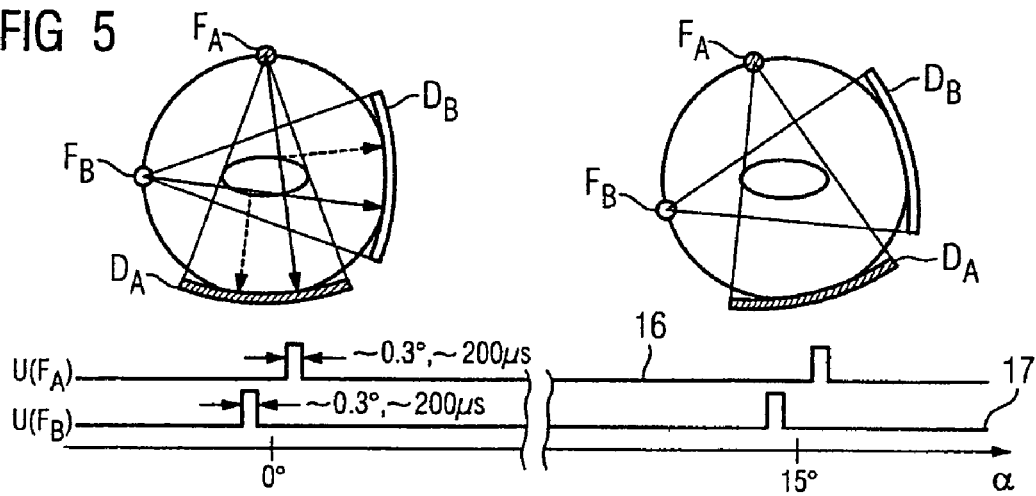
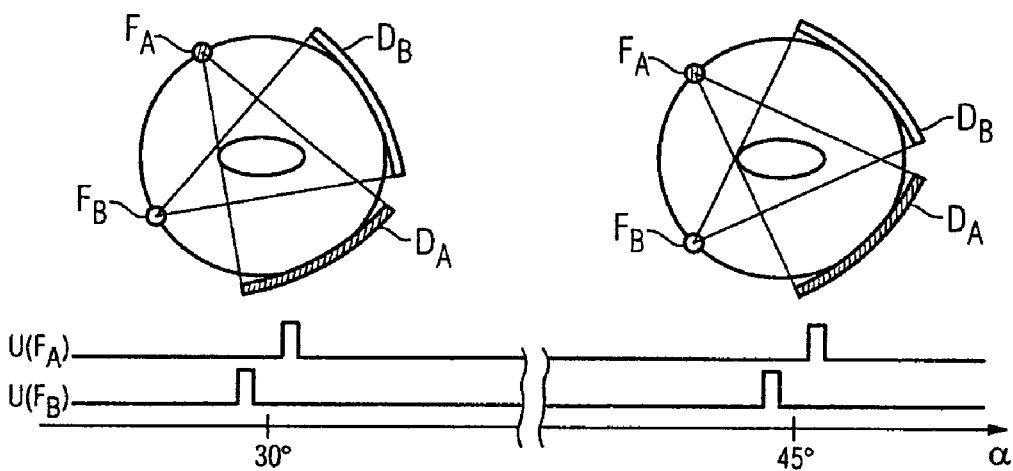
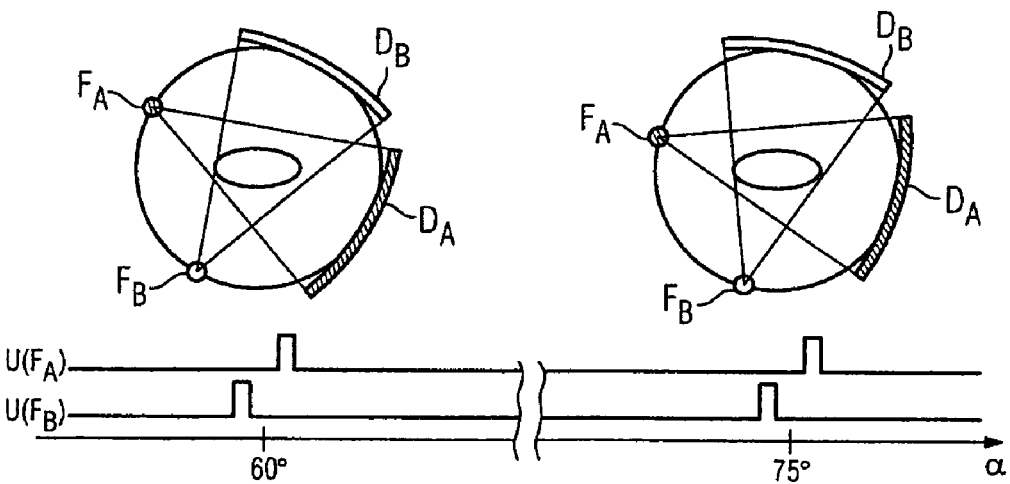

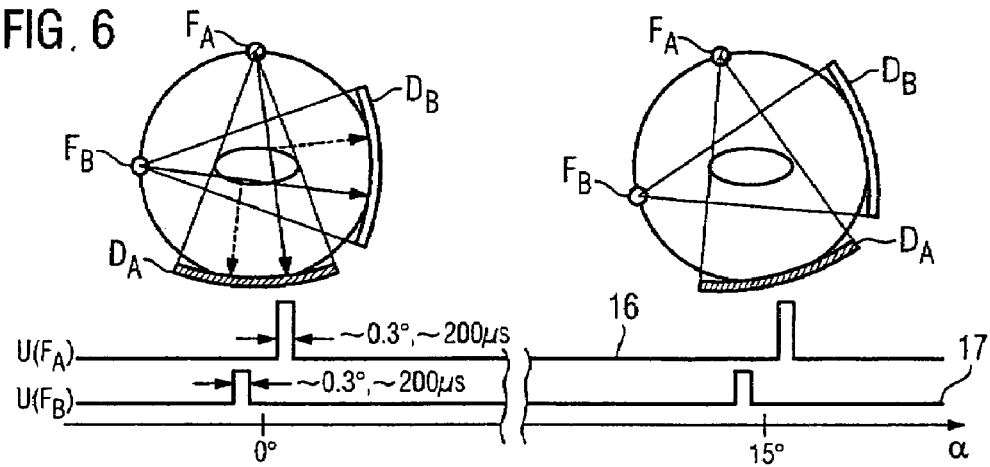
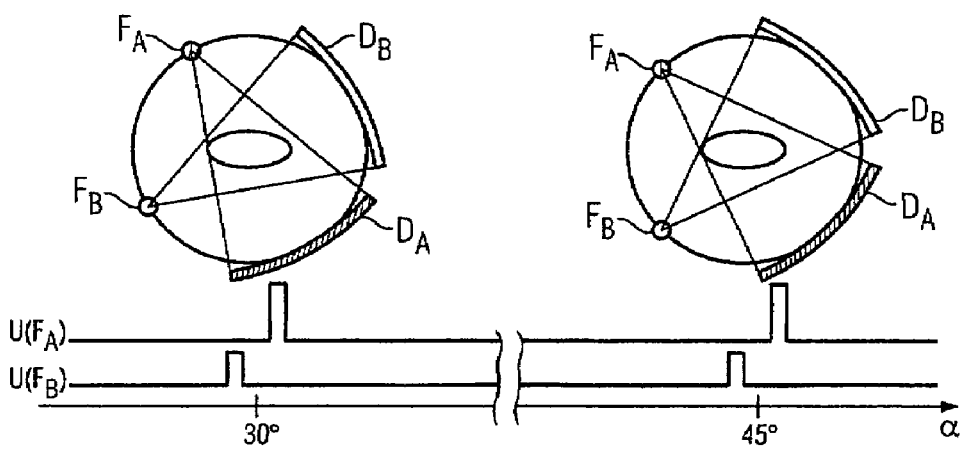
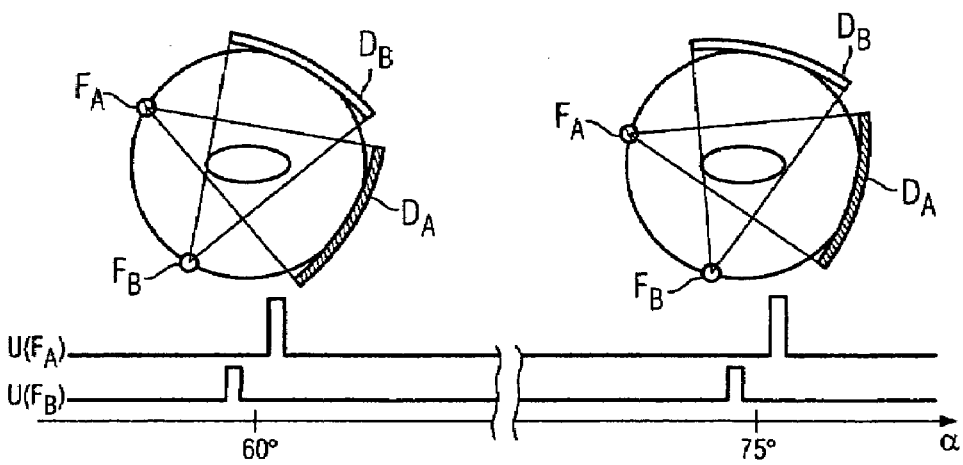

FIG 7
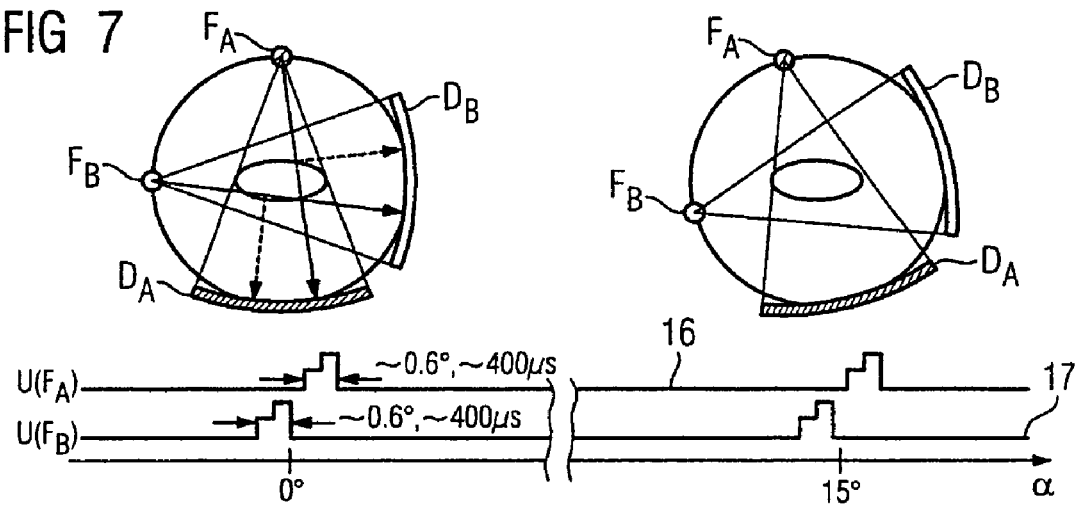
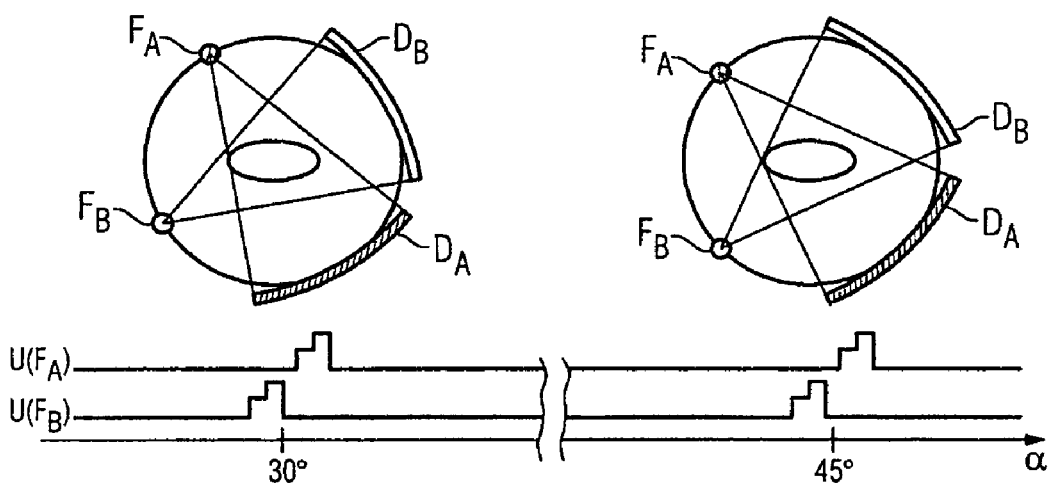
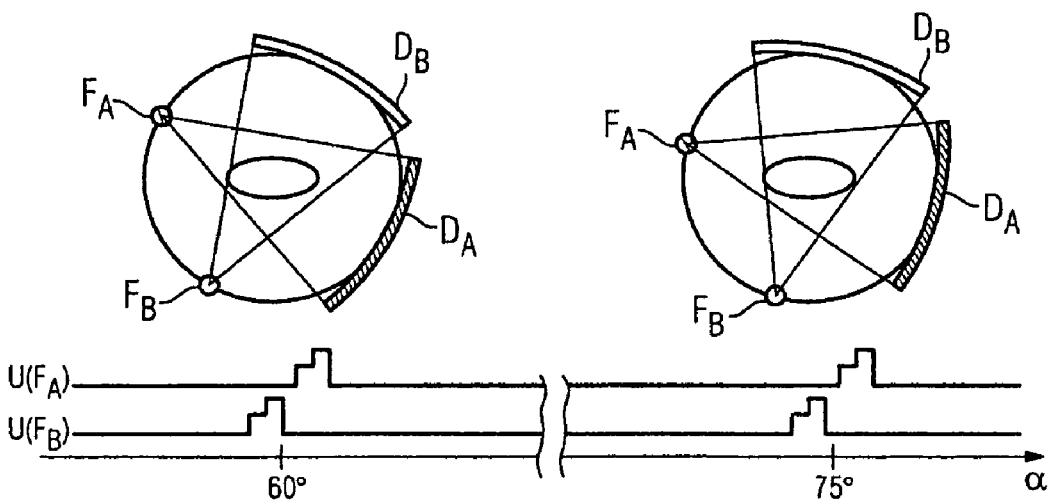

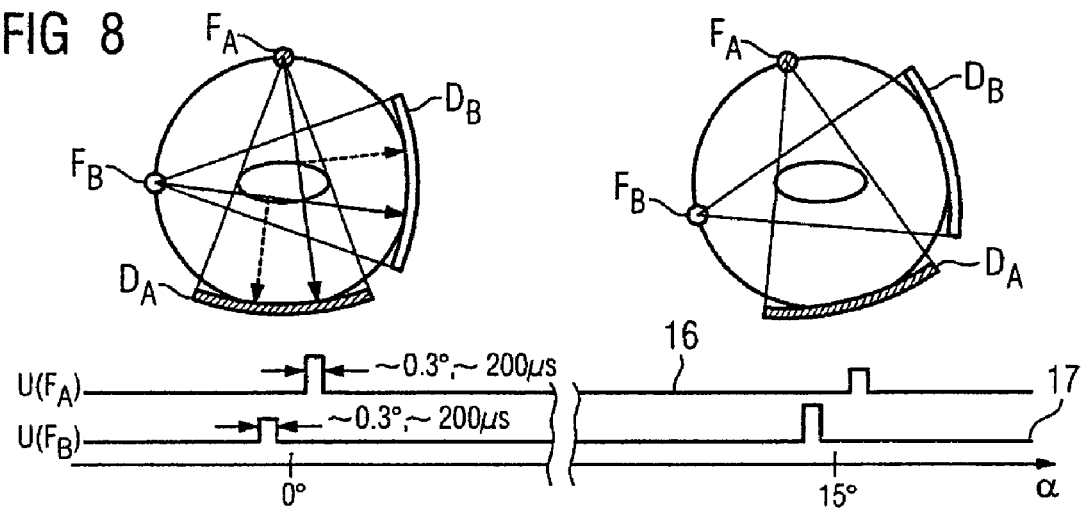
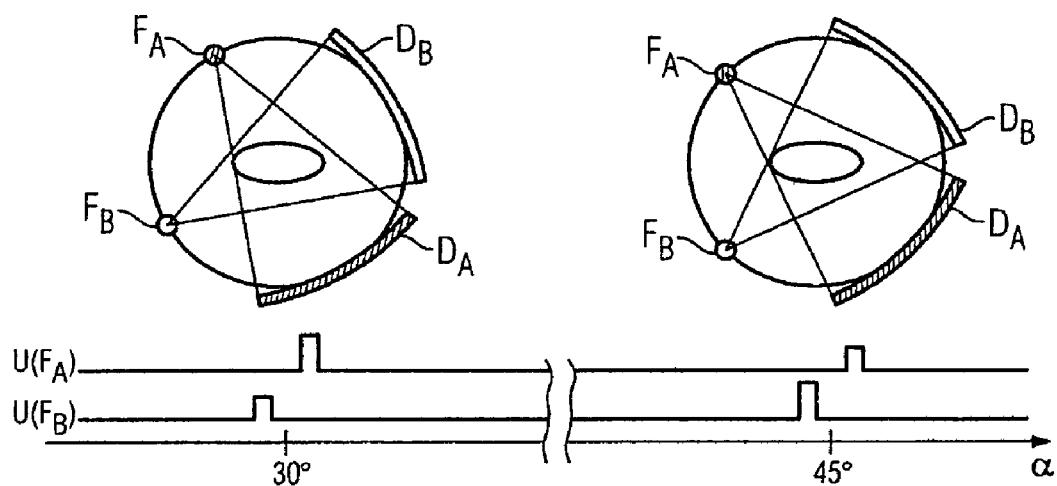
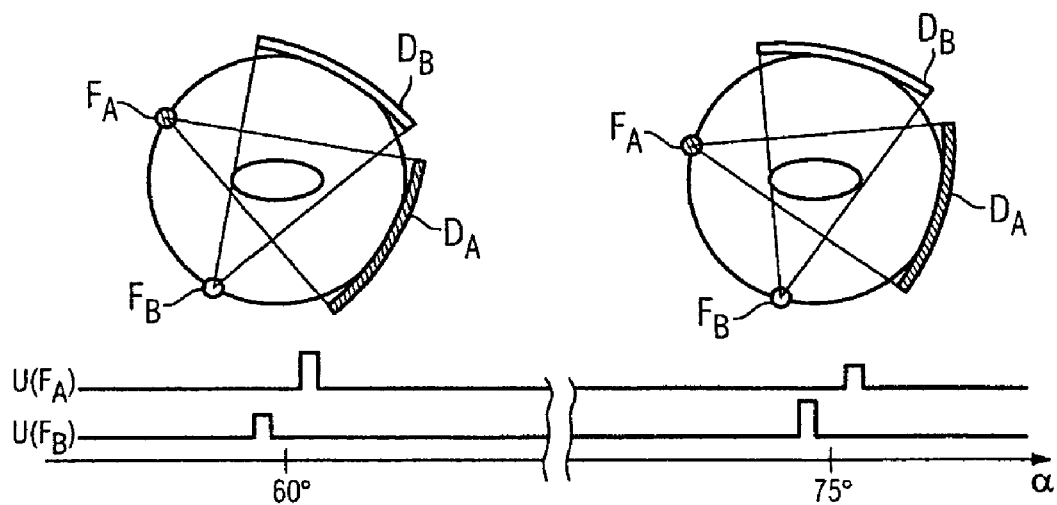
FIG 8

METHOD FOR PRODUCING TOMOGRAPHIC PICTURES WITH THE AID OF AN X-RAY COMPUTED TOMOGRAPHY SYSTEM WITH SCATTERED RADIATION CORRECTION

PRIORITY STATEMENT

The present application hereby claims priority under 35 U.S.C. §119 on German patent application number DE 10 2007 008 118.0 filed Feb. 19, 2007, the entire contents of which is hereby incorporated herein by reference.

FIELD

Embodiments of the invention generally relate to a method for producing tomographic pictures. For example, at least one embodiment may relate to a method for producing tomographic pictures with the aid of an X-ray computed tomography system including at least two X-ray sources that are arranged with an angular offset on a gantry and revolve around and scan an examination object in a fashion rotating about a system axis, in which case each of the at least two X-ray tubes form with, in each case, a set of oppositely situated detector elements or a co-rotating detector, a focus/detector combination by which during scanning the absorption of the emitted X-radiation through the examination object is determined, during scanning in the case of simultaneous operation of a number of focus/detector systems, scattered radiation that falsifies the measured values in the at least one other focus/detector system emanates from each focus/detector system, the scattered radiation is determined before the actual scanning, the measured data of the focus/detector systems are corrected at least with reference to the scattered radiation before the reconstruction of the tomographic picture.

BACKGROUND

Methods for producing tomographic pictures with the aid of a number of X-ray sources arranged with an angular offset on a gantry are fundamentally generally known, the person skilled in the art also being aware here of the problem of the scattered radiation occurring owing to the plurality of X-ray tubes being used simultaneously. At present there are two basically different variants for compensating or correcting this intensively occurring scattered radiation, specifically on the one hand by using a phantom to estimate the scattered radiation occurring either by measurement or by calculation and subsequently correcting the detector data with the scattered radiation values during the actual scanning. On the other hand, it is also known to measure the scattered radiation by various measures during the actual measurement on the actual examination object, and to undertake appropriate corrections.

In the first mentioned variant, the use of a phantom, the problem keeps arising that the measurements on the phantom, can reproduce the reality only approximately, and thus that any exact data relating to the scattered radiation can scarcely be available. It is also respectively to be considered here that the bearing of the examination object, that is to say generally a patient, with phantom conditions can be undertaken exactly only with difficulty, or it is also possible that a patient is wearing prostheses or implants that lead more intensely to scattered radiation that, of course, are not present in a generally valid phantom.

There are also fundamental attempts to obtain information with reference to the scattered radiation present during the actual scanning of the patient with the aid of a number of focus/detector systems. However, there is a problem here that there is additionally generally a need to use a relatively high radiation dose, since it is scarcely possible to carry out a rapid change in the dose rate of the X-ray tubes used without changing the acceleration voltage, and thus measurements required briefly during scanning are carried out exclusively with a single tube, as a rule with a full dose rate. A relatively high dose rate is thereby used for measuring the scattered radiation.

SUMMARY

At least one embodiment of the invention is directed to a method that, on the one hand, carries out a measurement of scattered radiation at the actual examination object and, on the other hand, in this case requires as low as possible a dose commitment for the examination object. Moreover, in accordance with a further aspect of at least one embodiment of the invention, it should also be possible to employ the dose rate used in a different way in order to determine the scattered radiation distribution.

The inventors have realized, in at least one embodiment, that in conjunction with a minimum error bandwidth the dose uptake ratio is most favorable when pilot scanning or pre-scanning in which the X-ray sources are operated singly and alternately is carried out before the actual scan for scanning with a number of focus/detector systems, the X-ray sources overall outputting no radiation dose for the majority of the revolution, that is to say the individual radiation sources are switched on in the manner of a flashlight only at specific recording angles, and the scattered radiation being measured respectively in the detectors not associated therewith. It has emerged in this case that relatively few measurements over the circumference suffice in order to detect the scattered radiation profile, that is to say the scattered radiation distribution in space, with sufficient accuracy. It is helpful in this case when additional lowpass filters are used that filter out the statistical fluctuations of the measurement.

Moreover, in this variant of the scanning the dose rate of the X-ray tubes can be greatly reduced without influencing the measuring accuracy. Furthermore, it is possible when performing such a pre-scan to combine the latter with the obligatory recording of a topogram, the topogram being carried out here by a juxtaposition of a multiplicity of individual recordings at the same rotation angle of the gantry, respectively offset in the z-direction.

In accordance with the basic ideas outlined above, the inventors propose a method, in at least one embodiment, for producing tomographic pictures with the aid of an X-ray computed tomography system that includes at least two X-ray sources that are arranged with an angular offset on a gantry and revolve around and scan an examination object in a fashion rotating about a system axis, in which case each of the at least two X-ray tubes form with, in each case, a set of oppositely situated detector elements or a co-rotating detector, a focus/detector system by which, during scanning, the absorption of the emitted X-radiation through the examination object is determined, during scanning in the case of simultaneous operation of a number of focus/detector systems, scattered radiation, that falsifies the measured values in the at least one other focus/detector system, emanates from each focus/detector system, the scattered radiation is determined before the actual scanning, the measured data of the focus/detector systems are corrected at least with reference to the scattered radiation before the reconstruction of the tomographic picture.

According to at least one embodiment of the invention, in accordance with the proposal of the inventors, this abovementioned method is improved by carrying out pre-scanning, in which:

the X-ray sources rotate about the examination object and the dose rate is modulated as a function of the rotation angle, no radiation dose is output over the majority of the revolution, at specific pre-scan angles a dose rate is produced briefly and individually in each case by the X-ray sources of the focus/detector systems, and the received scattered radiation is measured simultaneously by the detectors of the at least one other focus/detector system.

It is possible to use this method to keep the dose rate for measuring the scattered radiation during scanning very low and, at the same time, to determine the scattered radiation distribution with sufficient reliability on the object actually to be scanned immediately thereafter.

The method is particularly advantageous when, in conjunction with the pre-scanning, not only the scattered radiation is measured but additionally, at least one pre-scan angle, also the absorption of the examination object is measured, and a topogram is produced for this at least one pre-scan angle.

It is also possible with the aid of this method to produce a topogram at each pre-scan angle such that topograms from different directions are available in accordance with the number of the pre-scan angles used at which the X-ray tube is briefly in operation. For the operator, this results in an improved possibility for detecting the desired zone to be considered during the subsequent actual scan, and to define it with reference to its extent.

It is advantageous in this method when the pre-scan angles are distributed uniformly over the entire revolution. For example, 12, 24 or 48 pre-scan angles are used. However, it is pointed out that in the following analysis it is a question of the accuracy with which the scattered radiation distribution is to be recorded, more than 48 measurements for one revolution scarcely further leading to an improvement in the result.

As mentioned already, the inventors further propose, in at least one embodiment, that the recorded measured values of the scattered radiation can be smoothed with the aid of a lowpass filter in order to compensate possible statistical defects or measuring errors, it being possible, on the one hand, for the filtering to take place in a circumferential direction, but it is also possible to have filtering in a z-direction, on the other hand. There is basically also the possibility of using a two-dimensional filter for this type of filtering.

It is possible furthermore, that unmeasured intermediate values can be calculated by interpolation on the basis of the available measured values of the scattered radiation.

In an advantageous variant of at least one embodiment of the method, on times of the radiation sources are controlled during pre-scanning in such a way that the sum of the beam time is smaller than 2% of the duration of the entire pre-scan. Moreover, pre-scanning is preferably carried out for the reconstruction at a dose rate of at most 20%, preferably at most 10% of the power of the scan.

The inventors, in at least one embodiment, also propose that for pre-scanning only a portion of the determined detector data is used for determining scattered radiation. For example, the detector elements of the detector can be used in accordance with the black or the white squares on a chessboard, the computer time required thereby being substantially reduced. Furthermore, pre-scanning can be carried out with a sequential feed, that is to say a gantry rotation by 360° is carried out, after which a feed by a specific value is performed and after which, in turn, a circular scan about 360° is carried out. However, it is also alternatively possible to use a continuous feed by carrying out spiral scanning.

If it is intended to measure the scattered radiation field exclusively, it is also possible to select the feed such that it is greater than the detector width, so that there are produced between the individual measurements gaps that can, however, be relatively reliably intermediately interpolated on the basis of the relatively low frequency of change in the scattered radiation.

It is generally known that measurements can be carried out with different spectra, if appropriate even simultaneously, in X-ray CT systems with a number of focus/detector systems. Since the scattered radiation distribution is also dependent on the following X-ray spectrum to a certain degree, it is advantageous likewise to measure the spatial distribution of the scattered radiation during pre-scanning with the use of different X-ray spectra precisely in the case of such X-ray CT systems. In order to carry this out with the aid of a single pre-scan, the inventors additionally propose that the scattered radiation distribution is also produced and determined during the described pre-scan with the aid of different radiation spectra.

In the particular variant of an embodiment of the method, the inventors propose that during pre-scanning each focus/detector system uses another X-ray spectrum. This will advantageously be the X-ray spectrum actually used in each case during the subsequent scanning.

However, it is also alternatively possible for each focus/detector system to use at least two different X-ray spectra alternately during pre-scanning. If measurement is carried out in this way, after measurement there is a complete data record relating to the spatial distribution of the scattered radiation based on different X-ray spectra. It is thereby possible to use the respectively assigned or respectively appropriate scattered radiation distribution with reference to the correction of scattered radiation during later scanning, in accordance with the X-ray spectrum actually used while scanning.

In accordance with a further aspect of an embodiment of the invention, it is further proposed also to make use of the absorption data determined from pre-scanning for optimum dose modulation of the X-ray sources for the actual scan. The aim in the case of such dose modulation is respectively to set the dose rate of the radiation sources so as to attain on the detector side precisely the dose rate required for optimum imaging in conjunction with the lowest possible dose commitment for the examination object.

To this end, the inventors thus propose, in at least one embodiment, that a dose modulation dependent on angle and z-position is calculated for the X-ray sources used in accordance with knowledge of the absorption of the examination object measured during pre-scanning at least two pre-scan angles, this being done in such a way that during actual scanning dose rate values that are as uniform as possible are produced independently of the angle of the radiation sources on the detector side after transirradiation of the examination object.

In order, if possible, to make use of all the dose output to the examination object, it appears particularly favorable also to measure the absorption of the examination object at all pre-scan angles at which the scattered radiation is measured, and to calculate the dose modulation of the radiation sources from the absorption values of the examination object obtained from different scan angles.

If different energy spectra are used for pre-scanning and scanning, it is particularly favorable also to determine the dose modulation specifically in relation to the energy spectrum used for the radiation, and also to use a specific dose modulation in the actual scan. Thus, the dose modulation of a low energy radiation will turn out to be stronger than in the case of a high energy radiation on the basis of the different absorption properties of the radiation.

In accordance with this inventive method and its previously described embodiments, the inventors also propose, in at least one other embodiment, an X-ray CT system having at least two focus/detector systems and an arithmetic and control unit with a memory for program code, there being stored according to an embodiment of the invention in the memory of the arithmetic and control unit program code that carries out during operation the method steps of the method outlined above.

BRIEF DESCRIPTION OF THE DRAWINGS

The invention is described in more detail below using the example embodiments and with the aid of the figures, only the features required for understanding embodiments of the invention being illustrated. The following reference numerals are used here: 1: X-ray computed tomography system; 2: first X-ray tube (system A); 3: first detector (system A); 4: second X-ray tube (system B); 5: second detector system (system B); 6: gantry housing; 7: patient; 8: displaceable patient couch; 9: system access; 10: control and computation unit; 11: memory; 12: profile of the dose rate of the scattered radiation in the detector 5; 13: profile of the dose rate of the scattered radiation in the detector 3; 14: beam cones of the X-ray tube 2 in relation to the detector 3; 15: beam cones of the X-ray tube 4 in relation to the detector 5; 16: profile of the acceleration voltage ($F_A$); 17: profile of the acceleration voltage ($F_B$); 18: spiral path of the X-ray tube; 19: profile of the absorption of the patient in the lateral direction; 20: profile of the absorption of the patient in a coronary direction; 21: profile of the modulated dose rate; $I_{R(Z)}$: modulated tube current; $S_1$-$S_4$: axial sections of the patient; $T_{lateral}$: lateral topogram; $T_{a.p.}$: topogram in the anterior-posterior direction.

In detail:

FIG. 5: shows a schematic of the scanning situation for the purpose of determining scattered radiation, with specification of the profile of the acceleration voltage in two focus/detector systems given a uniform acceleration voltage;

FIG. 6: shows a schematic of the scanning situation for the purpose of determining scattered radiation, with specification of the profile of the acceleration voltage in two focus/detector systems given different acceleration voltages per detector system;

FIG. 7: shows a schematic of the scanning situation for the purpose of determining scattered radiation, with specification of the profile of the acceleration voltage in two focus/detector systems with two different acceleration voltages per focus/detector system;

FIG. 8: shows a schematic of the scanning situation for the purpose of determining scattered radiation, with specification of the profile of the acceleration voltage in two focus/detector systems with different acceleration voltages per scan angle, in an alternating fashion for consecutive scan angles;

DETAILED DESCRIPTION OF THE EXAMPLE EMBODIMENTS

Figure 1:
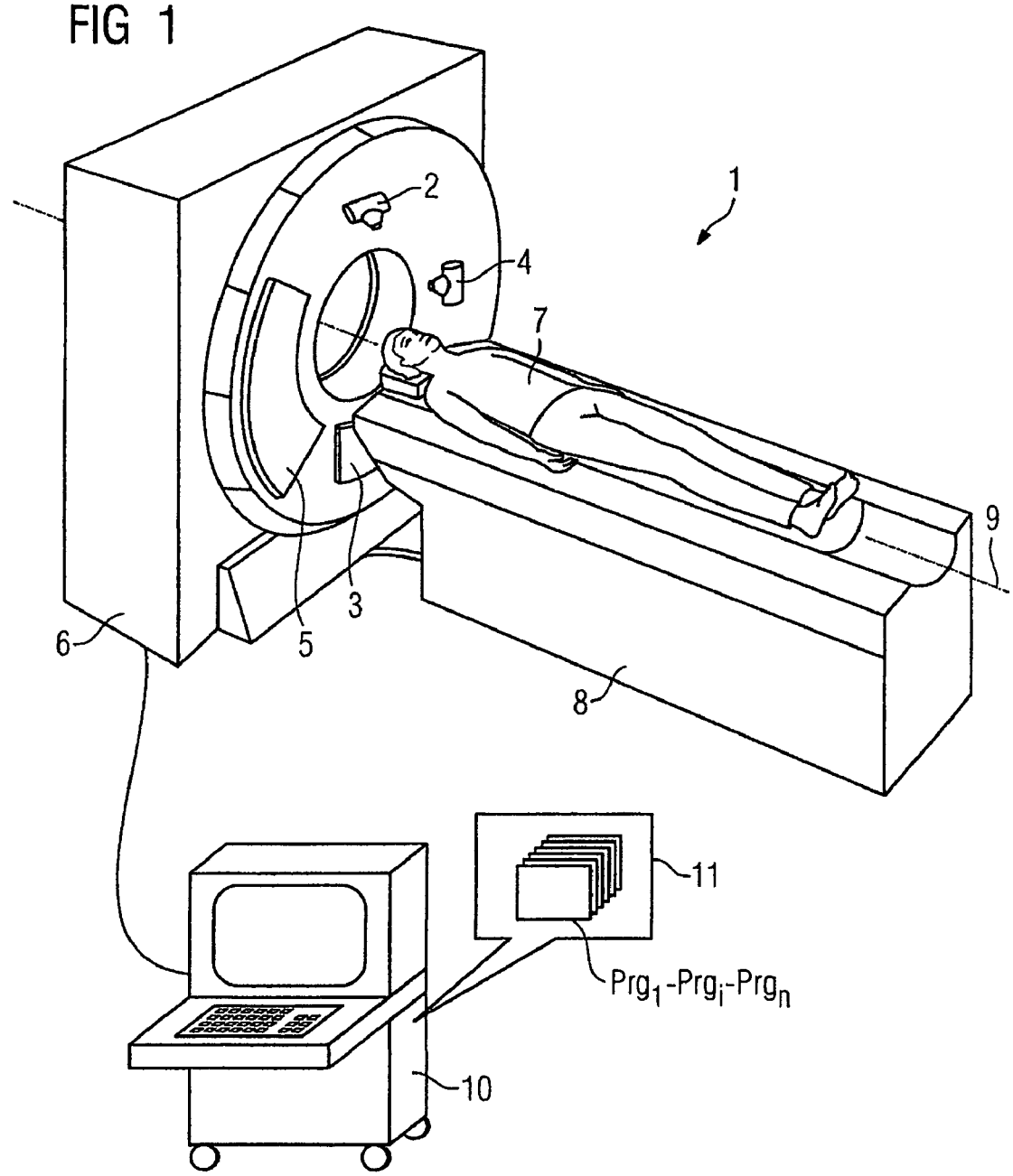
FIG. 1: shows a 3D schematic of a CT system having two focus/detector systems.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows an inventive CT system 1 having two focus/detector systems that are arranged on a gantry with a 90° angular offset. The gantry is located in the gantry housing 6, the first focus/detector system being formed by the X-ray tube 2 and the oppositely situated detector 3, while the second focus/detector system is formed by the X-ray tube 4 with the oppositely situated detector 5. In the example selected and also in the examples illustrated later, the X-ray tubes and the detector systems are respectively fastened on the gantry and rotate in common about the system axis 9.

It is, however, pointed out that this is only an example illustration and an example design of an example embodiment of a CT system. An example embodiment of the invention can be carried out equally well with focus/detector systems in which the X-ray tube is arranged on a rotating gantry, while the detector comprises a stationary detector ring running round 360°. Both variants can be used in the scope of an example embodiment of the invention, a focus of an X-ray tube respectively being regarded as focus/detector system in a fashion including the detector element, situated opposite this focus, of the detector that are used to measure the absorption of the patient.

A patient 7 lies as examination object on a longitudinally movable patient couch 8 that can be pushed along the system axis 9 into the measuring field or through the measuring field of the CT system. This can be done either continuously as simultaneous rotation of the focus/detector systems, or sequentially for circular scanning.

Illustrated schematically in addition in FIG. 1 is the control and computation unit 10, which is used to control the functioning of the CT system and record detector data that are subsequently fed to a reconstruction calculation in order to obtain tomographic data. To this end, program code is stored in the form of computer programs $Prg_1$ to $Prg_n$ in the memory 11, illustrated schematically, of the control and computation unit 10 that is executed in the operation if required and, if appropriate, also carries out the method steps according to an embodiment of the invention.

In the following FIGS. 2 to 4, the problem of scattered radiation in the case of a number of focus/detector systems arranged with an angular offset from one another is described in more detail on the example of two focus/detector systems arranged with an angular offset of 90°.

Figure 2:
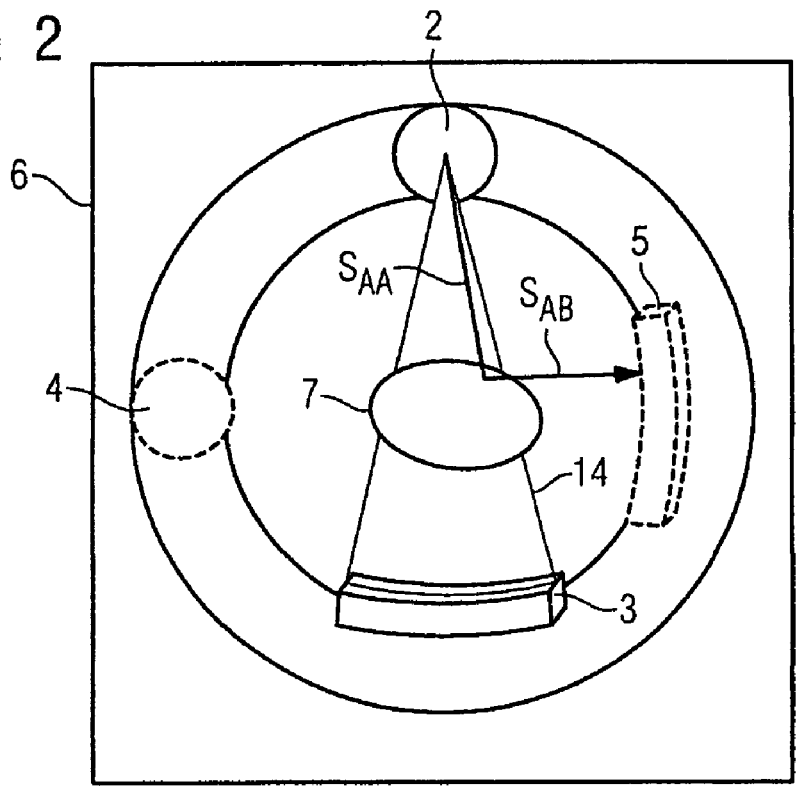
FIG. 2: shows a sectional illustration of a CT system having two focus/detector systems, with an illustration of the direct radiation and the scattered radiation of the first focus/detector system.

FIG. 2 shows a cross section through a gantry at the level of the focus/detector systems, the first focus/detector system being illustrated with an X-ray tube 2 and the oppositely situated detector 3, and the second focus/detector system being illustrated by the X-ray tube 4 and the oppositely situated detector 5. Both focus/detector systems are located on the gantry inside the gantry housing 6. Located in the measuring field of the focus/detector system is a patient 7 who is transirradiated by the operating X-ray tube 2 with a beam cone 14. Illustrated for the purpose of illustrating the scattered radiation is a beam $S_{AA}$, emanating from the focus of the focus/detector system A (formed by the X-ray tube 2 and the oppositely situated detector 3), and the scattered beam $S_{AB}$, which is produced by this beam and is measured on the detector 5 of the focus/detector system B (illustrated by the X-ray tube 4 and the oppositely situated detector 5).

In FIG. 2, the X-ray tube 4 of the focus/detector system B is not in operation, and so it is only the scattered radiation, which emanates through the focus detector A that is detected in the detector 5 of the focus/detector system B.

Figure 3:
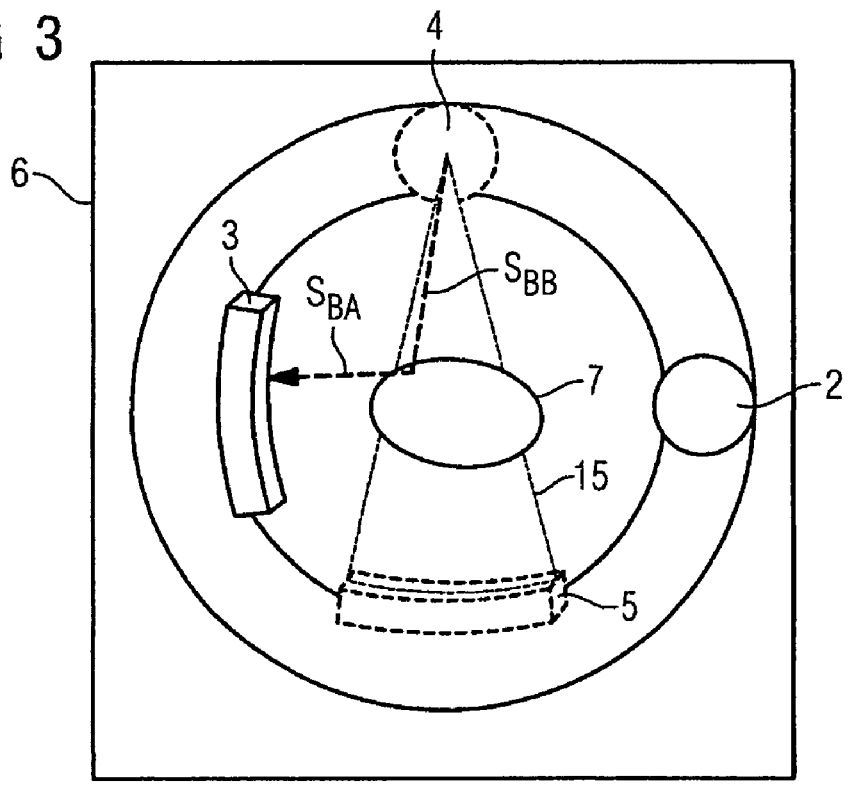
FIG. 3: shows a sectional illustration of a CT system having two focus/detector systems with an illustration of the direct radiation and the scattered radiation of the second focus/detector system at the same angular position as in FIG. 2.

FIG. 3 shows the same gantry as in FIG. 2. After a 90° rotation, the focus/detector system A is located at the same position as in the focus/detector system A in FIG. 2. Here, as well, it is shown how the now operating focus/detector system A uses the X-ray tube 4 to cast a beam cone 15 through the patient 7, for explanation purposes, an individual direct beam $S_{BB}$ here also striking the edge region of the patient 7 and producing the scattered radiation in the form of the beam $S_{BA}$ that is incident on the detector 3 of the focus/detector system A.

Figure 4:
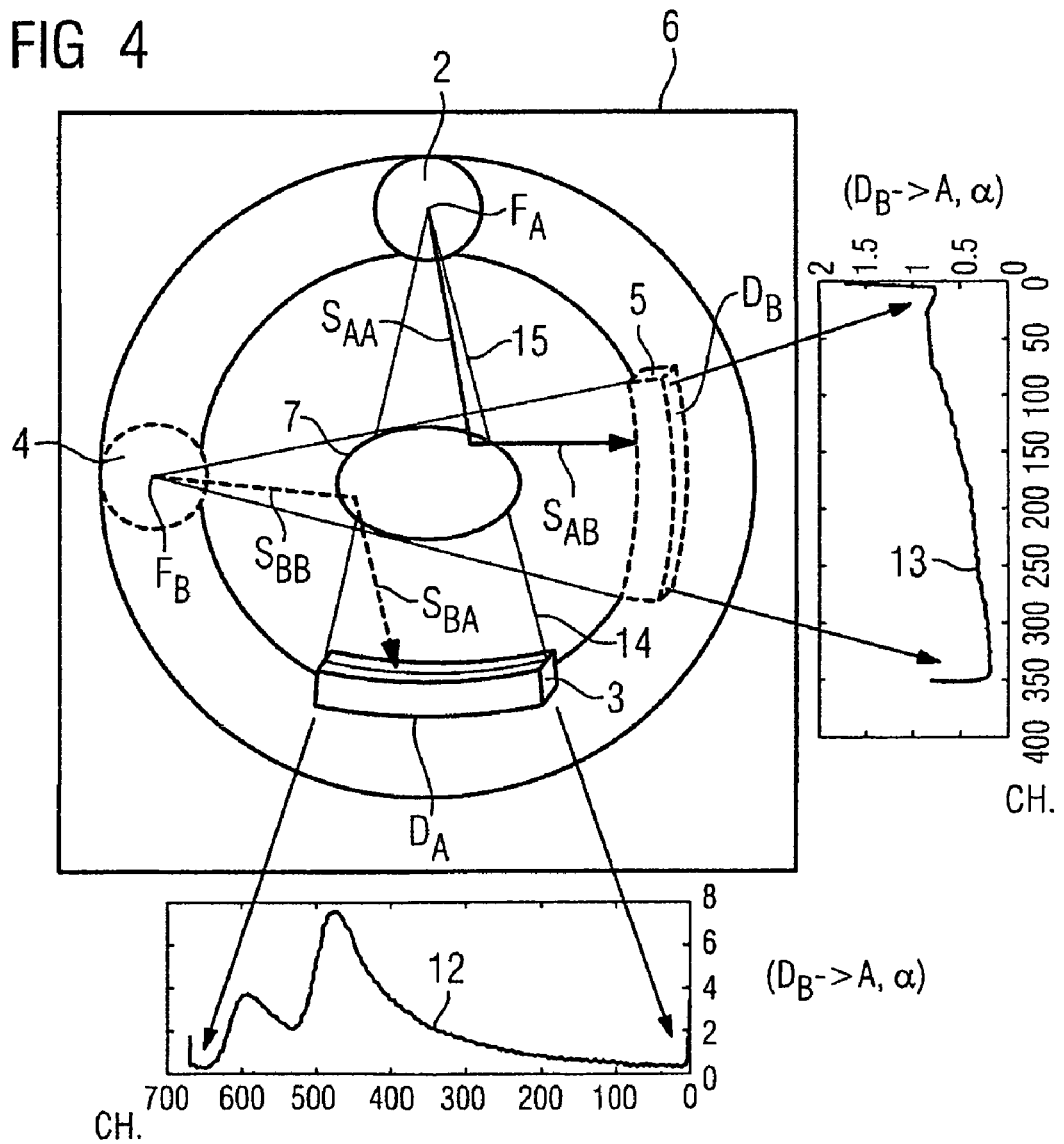
FIG. 4: shows a cross section through a gantry having two focus/detector systems and an illustration of the scattered radiation distribution for the two detector systems.

A situation such as is illustrated in FIG. 4 arises from now considering the scattered radiations produced by the entire beam cones in the respective other detector system. Here, the profile of the scattered radiation intensity is illustrated in the curves 12 and 13, respectively, in a respectively assigned graph for a detector row, this being done for a specific rotation angle in the case of which the X-ray tube 2 is located in the 12 o'clock position, and the X-ray tube 4 in the 9 o'clock position. The assignment of the curves 12 and 13, respectively is given by the connecting arrows between the detectors and the curves.

Considering the curve 12, which illustrates the scattered radiation received in the detector 3 by way of the radiation produced by the X-ray tube 4, it is seen that the detector channels are plotted on the abscissa while the ordinate shows the dose rate of the radiation received in the focus/detector system B from the focus/detector system A given a rotation angle α of the gantry as indicated here. Correspondingly the detector channels Ch. of the detector 5 are shown on the ordinate in the graph arranged at right angles, while, once again, the ordinate of this coordinate system rotated by 90° with respect to all other illustrations illustrates the dose rate of the scattered radiation, coming from the focus/detector system B on to the focus/detector system A, given the same rotation angle α of the gantry.

It is to be noted in this case that the two scattered radiation profiles 12 and 13 were not recorded at exactly the same time, but that during recording it is respectively only the X-ray tube of the respective other focus/detector system that is in operation and so, no direct radiation is incident on the associated detector.

FIGS. 5 to 8 show various example different timing responses of the operation of the respective X-ray tubes, with the aid of which the respective scattered radiation is scanned in a way according to an embodiment of the invention, it being pointed out that in addition to the measurement of scattered radiation it is also possible to evaluate the detector respectively situated opposite the operating focus, in order to obtain direct absorption values of the patient at the respective rotation angle of the gantry, and thereby to be able to produce a topogram.

In accordance with a further aspect of an embodiment of the invention, such a simultaneous absorption measurement during the determination of the scattered radiation can also be used to determine an optimized dose rate modulation of tube current modulation.

FIGS. 5 to 8 respectively show six selected rotary positions, differing from one another by 15°, of the gantry between 0° and 75°, and, thereunder, the profile of the acceleration voltages $U(F_A)$ and $U(F_B)$ of the respective focus of the focus/detector system A or B, respectively. It is to be seen from the curves of the acceleration voltage that the focus/detector systems A and B respectively have a voltage jump of the same height at the positions 0°, 15°, etc. for a short time, specifically the duration of a read-out cycle of the respective detector. In the case of CT systems currently in operation, in the case of which approximately 1152 read-buts of the detector system take place over a revolution, the revolution time lasting approximately 300 ms, the duration of a voltage jump is respectively approximately 200 µs, corresponding to a rotation angle of approximately 0.3°. As is to be seen from the profile of the voltage curves 16 and 17, the focus/detector systems respectively operate reciprocally, and so the scattered radiation produced can be measured respectively without distortion in the respective other focus/detector system.

As is to be seen from FIG. 5, this measurement is carried out at the predetermined pre-scan angles $\alpha_i$ of the gantry, specifically at 0°, 15°, 30°, 45°, etc. such that the scattered radiation given the use of a very low dose is known over the entire revolution of 360° at 24 positions of the gantry, since only very short settling times are used. According to an embodiment of the invention, a lowpass filter can now be laid over the measured scattered radiation distribution such that possible statistical fluctuations are compensated. The scattered radiation values can be interpolated at the unmeasured positions. It may be remarked with reference to the filtering that the latter can be carried out on the one hand at the respective position along the detector lines and/or detector rows.

Whereas in FIG. 5 the two focus/detector systems A and B with the focuses $F_A$, $F_B$ and the detectors $D_A$ and $D_B$ were operated with the same acceleration voltage and the same X-ray spectrum, FIG. 6 shows an illustration corresponding to FIG. 5 but here use has respectively been made in the two focus/detector systems of another acceleration voltage $U(F_A)$ or $U(F_B)$, respectively, of different size. Accordingly, the scattered radiation produced by different X-ray spectra is also measured in two focus/detector systems at the angular positions at which the scattered radiation is measured. In this case, the respective topogram measured by the focus/detector system A or B is also determined with the aid of different X-ray spectra, as a result of which additional findings can result in relation to the inner structure of the examination object. It is to be borne in mind here that the X-ray tubes are respectively arranged with a rotational offset at each gantry position.

Appropriately enough, during such measurement of the scattered radiation with the aid of different acceleration voltages, in the focus/detector systems it is natural to carry out the subsequent examination with the aid of the same different acceleration voltages in the corresponding focus/detector systems.

FIG. 7 shows another variant of an embodiment in which, depending on the focus/detector system, in accordance with the profile of the curves 16 and 17 of the acceleration voltage of the individual focus/detector systems, firstly a low acceleration voltage and thereafter a higher acceleration voltage are sequentially switched in each focus/detector system for each voltage per corresponding scattered radiation distribution. Such a measurement now renders it possible during the later, actual scan either also to be able to run different acceleration voltages there alternately in the individual focus/detector systems, and respectively to use the correct scattered radiation distribution according to the respectively used radiation spectrum in order to correct the scattered radiation. However, it is to be noted in this regard that the dose commitment during pre-scanning is approximately twice as high for determining the scattered radiation distribution than in the case of the use of a single radiation spectrum per focus/detector system.

Yet another design variant is illustrated in FIG. 8. Here, different acceleration voltages are used alternately in a focus/detector system, each focus/detector system operating its X-ray tube only for a single measuring cycle depending on the angular positioning of the gantry thereof, and an alternating voltage being used from measuring cycle to measuring cycle.

Overall, an embodiment of this inventive method can now be used to determine exactly the actual scattered radiation distribution on the object to be scanned, the dose used to this end remaining exceptionally low, and it also being possible simultaneously to use the dose rate for producing topograms. Consequently, there is also no need to waste unnecessary time with reference to the work sequence in order to produce the scattered radiation distribution while this can subsequently concentrate exclusively on determining the absorption values during the actual scan.

In addition to determining the scattered radiation and to the production, running parallel thereto, of a number of topograms in a different direction, it is also possible to optimize the adaptation of the dose modulation of the X-ray tubes on their path around the patient by means of an absorption measurement during pre-scanning. The following FIGS. 9 to 12 serve to illustrate this aspect.

Figure 9:
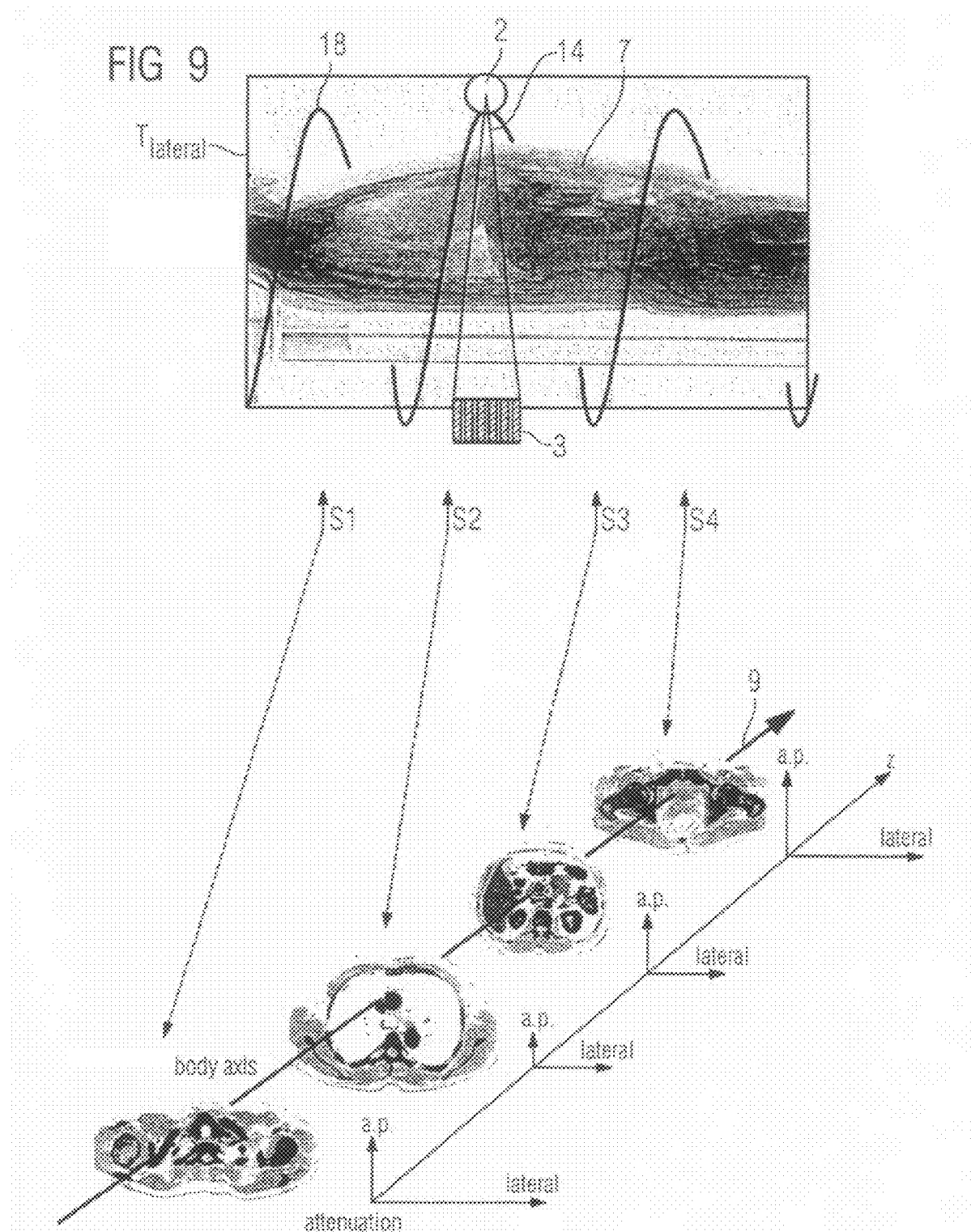
FIG. 9: shows an illustration of the scanning of an X-ray tube and of the measured absorption.

Shown at the top in FIG. 9 is a laterally recorded topogram $T_{lateral}$ in which the path 18 of an X-ray tube 2 around the patient 7 is shown with the inclusion of the oppositely situated detector 3 and the associated beam cone 14. Shown under this topogram are three exemplary sections S1 to S4 with reference to their z-position. The associated tomograms are represented pictorially therebelow—along the system axis 9—it being evident that the cross sections fundamentally have different extents in an axial plane. Correspondingly, the absorption at the corresponding z-positions of the patient is also fundamentally different. In addition to the sections S1 to S4 these different absorptions are illustrated laterally in the AP direction by the arrows, the length of these arrows corresponding to the respective magnitude of the absorption. Thus, it is to be seen that in the first section S1 very high absorption is present in the shoulder region in the lateral direction at the level of the patient 7 illustrated in the topogram, where relatively low absorption is present in the sagittal or AP direction owing to the slight extent in this direction.

Subsequently following are the section S2 through the lung, thereafter a section S3 through the abdomen and a section S4 in the region of the pelvic girdle. The different absorption in a lateral or AP direction is illustrated by the length of the arrows next to the sections in each case. This clearly demonstrates that—depending on the position and direction of radiation of the X-ray tube—there should rationally also be different dose rates present at the X-ray tube in accordance with these different absorptions, such that approximately equal absorptions are present in each case on the side of the detector after transirradiation of the patient, and the detector is struck by the beam cone with approximately the same dose rate. A largely similar signal-to-noise ratio also results correspondingly. It is self-evident that there is a need during the scanning with a modulated tube current to consider modulation of the initial dose rate $\dot{D}_o$ of the X-ray tube when calculating the subsequent absorption values into the ratio of measured dose to initial dose $D/D_0$. This can take place, for example, by means of corresponding monitor detector elements or knowledge of the relationship between the tube current and dose rate of the X-ray tube during measurement of the tube current.

Figure 10:
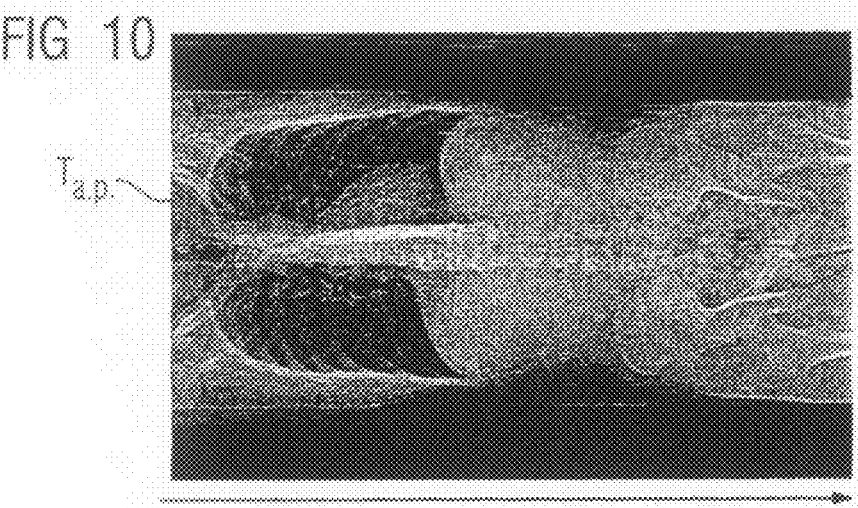
FIG. 10: shows an illustration of topogram of a patient in the anterior-posterior direction.

Undertaking such dose rate modulations or tube current modulations is known in principle in the prior art, but this modulation is presently undertaken substantially on the basis of knowledge of a topogram in one direction, as a rule a topogram $T_{a.p.}$ in the AP direction, as is illustrated in FIG. 10, the actually measured absorption being used approximately in the AP direction when recording the topogram $T_{a.p.}$, and the absorption in the lateral direction additionally being calculated back by summing up the absorption values from the topogram $T_{a.p.}$ in the lateral direction.

Figure 11:
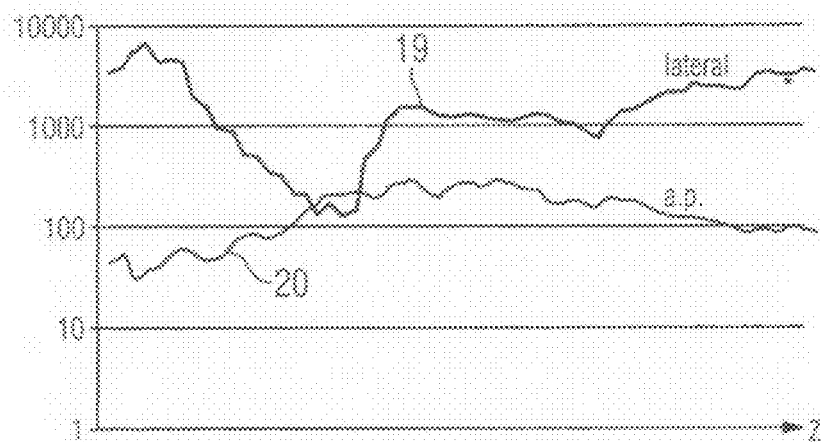
FIG. 11: shows a profile of the absorption of a patient in the lateral direction and an anterior-posterior fashion above the z-axis.

The absorption values of the patient shown in FIG. 10 are illustrated in FIG. 11 along the z-axis plotted in the abscissa. The absorption values are plotted in logarithmic form on the ordinate. Thus, the curve 19 in this diagram shows the profile of the absorption over z measured in the lateral direction, while the curve 20 illustrates the profile of the absorption over z in the AP direction.

Figure 12:
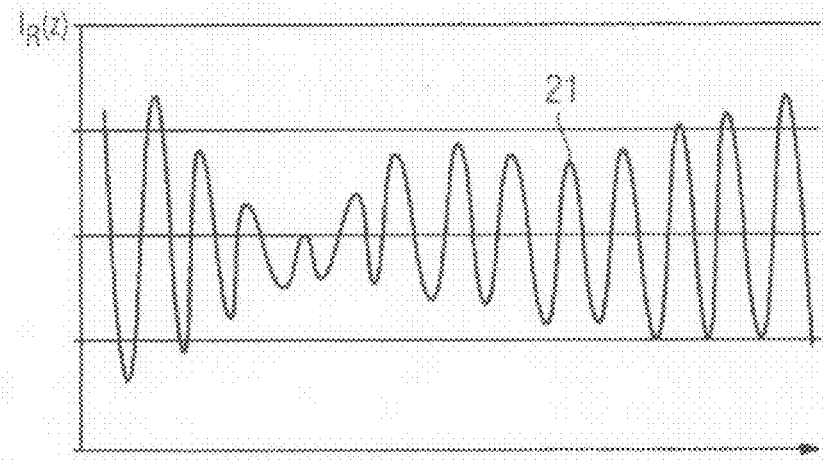
FIG. 12: shows an inventively modulated tube current $I_R(Z)$ above the z-axis.

The modulation of the dose rate or the modulation of the tube current $I_{R(Z)}$ is shown in FIG. 12 in accordance with this varying absorption in different directions. Because of the spiral revolution of the X-ray tube about the patient, the dose rate, or the tube current shown here, thus fluctuates to and fro in an approximately sinusoidal shape between the values that correspond to the lateral absorption direction corresponding to the curve 19 from FIG. 11—and the values that correspond to the absorption in the AP direction—corresponding to the curve 20 in FIG. 11—the same radiation values subsequently coming up on average irrespective of the actual absorption at the detector. Such a profile of the tube current modulation in the case of spiral scanning is illustrated in the curve 21 of the figure.

Although in the illustrations of FIGS. 9 to 12 it is only the absorption and the tube current correspondingly required therefor, or the corresponding dose rate that is determined in two different directions, specifically lateral and anterior-posterior ones, it is also within the scope of at least one embodiment of the invention not only to measure the absorption of the patent in two directions when determining the scattered radiation distribution, but also to use a multiplicity, for example 12, 24 or 48 directions. This yields a substantially improved adaptation of the modulated dose rate in accordance with the actual absorption response of the patient as the X-ray tubes rotate during scanning. According to an embodiment of the invention, this measurement of the absorption response as a function of angle and position can also be determined with different energy spectra, and the dose rate modulation can be adapted as a function of the X-ray spectrum actually used.

Thus, owing to this aspect of an embodiment of the invention, the overall result in the case of pre-scanning, in which the scattered radiation correction is determined primarily without an additional increase in the radiation dose for the patient, is to find an optimum dose modulation that leads overall to further minimization of the dose commitment required during the actual scan and which is necessary for recording CT images.

It goes without saying that the features of embodiments of the invention that have been mentioned above can be used not only in the combination respectively specified, but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing tomographic pictures with the aid of an X-ray computed tomography system including at least two X-ray sources, arranged with an angular offset on a gantry to revolve around and scan an examination object in a fashion rotating about a system axis, each of the at least two X-ray sources together with at least one of respective detector elements and a respective co-rotating detector constituting a focus/detector system, the method comprising:

determining absorption of emitted X-radiation through the examination object, during scanning using the at least two focus/detector systems;

determining scattered radiation, wherein during scanning, scattered radiation emanates from at least one of the at least two focus/detector systems and falsifies measured values in another of the at least two focus/detector systems;

correcting measured data of the focus/detector systems, at least with reference to the scattered radiation, before the reconstruction of the tomographic picture, wherein in order to determine a scattered radiation distribution, pre-scanning is carried out in which:

the X-ray sources rotate about the examination object and a dose rate is modulated as a function of the rotation angle, no radiation dose is output over the majority of the revolution, at specific pre-scan angles, a dose rate is produced briefly and individually in each case by the X-ray sources of the focus/detector systems, and the received scattered radiation is measured simultaneously by the detector of the another of the at least two focus/detector systems.

2. The method as claimed in claim 1, wherein, during pre-scanning, the absorption of the examination object is also measured at least one pre-scan angle and at least one topogram is produced.

3. The method as claimed in claim 2, wherein a dose modulation dependent on angle and z-position is calculated for the X-ray sources used in accordance with knowledge of the absorption of the examination object measured during pre-scanning at at least two pre-scan angles, this being done in such a way that during actual scanning dose rate values that are as uniform as possible are produced independently of the angle of the radiation sources on the detector side after transirradiation of the examination object.

4. The method as claimed in claim 3, wherein the absorption of the examination object is measured at all pre-scan angles at which the scattered radiation is measured, and the dose modulation of the radiation sources is calculated from the measured absorption values.

5. The method as claimed in claim 4, wherein the dose modulation is determined specifically in relation to the radiation energy spectrum used, and is used in the actual scan.

6. The method as claimed in claim 3, wherein the dose modulation is determined specifically in relation to the radiation energy spectrum used, and is used in the actual scan.

7. The method as claimed in claim 1, wherein the pre-scan angles are distributed uniformly over the entire revolution.

8. The method as claimed in claim 1, wherein measurement is performed each revolution at at least 12 pre-scan angles.

9. The method as claimed in claim 8, wherein measurement is performed each revolution at at least 24 pre-scan angles.

10. The method as claimed in claim 9, wherein measurement is performed each revolution at at least 48 pre-scan angles.

11. The method as claimed in claim 1, wherein the measured values of the scattered radiation are smoothed at least in one direction with the aid of a lowpass filter.

12. The method as claimed in claim 1, wherein the unmeasured intermediate values of the scattered radiation are interpolated.

13. The method as claimed in claim 1, wherein the on time of the radiation sources is controlled during pre-scanning in such a way that the sum of the beam time is smaller than 2% of the duration of the entire pre-scan.

14. The method as claimed in claim 1, wherein during pre-scanning measurement is performed for the reconstruction at a dose rate of at most 20% of the power of the scan.

15. The method as claimed in claim 14, wherein during pre-scanning measurement is performed for the reconstruction at a dose rate of at most 10% of the power of the scan.

16. The method as claimed in claim 1, wherein only a portion of the determined detector data is used for determining scattered radiation during pre-scanning.

17. The method as claimed in claim 1, wherein pre-scanning is carried out with the aid of a sequential feed.

18. The method as claimed in claim 17, wherein the sequential feed includes sequential scanning.

19. The method as claimed in claim 1, wherein the pre-scanning is carried out with the aid of a continuous feed (spiral scanning).

20. The method as claimed in claim 19, wherein the continuous feed includes spiral scanning.

21. The method as claimed in claim 1, wherein the pre-scanning is carried out with a feed that is greater than the detector width.

22. The method as claimed in claim 1, wherein, during the pre-scanning, the scattered radiation distribution is produced and determined with the aid of different radiation spectra.

23. The method as claimed in claim 22, wherein, during the pre-scanning, each focus/detector system uses another X-ray spectrum.

24. The method as claimed in claim 22, wherein, during the pre-scanning, each focus/detector system uses at least two different X-ray spectra alternately.

25. An X-ray CT system, comprising:
at least two focus/detector systems, each of the at least two focus/detector systems including an X-ray source and a detector; and
an arithmetic and control unit with a memory including program code, the program code, when executed in the arithmetic and control unit, for carrying out,
determining scattered radiation, wherein during scanning scattered radiation emanates from at least one of the at least two focus/detector systems and falsifies measured values in another of the at least two focus/detector systems;
correcting measured data of the focus/detector systems, at least with reference to the scattered radiation, before the reconstruction of a tomographic picture, wherein in order to determine a scattered radiation distribution, pre-scanning is carried out in which,
the X-ray sources of the at least two focus/detector systems rotate about the examination object and a dose rate is modulated as a function of the rotation angle,
no radiation dose is output over the majority of the revolution,
at specific pre-scan angles, a dose rate is produced briefly and individually in each case by the X-ray sources of the focus/detector systems, and
the received scattered radiation is measured simultaneously by the detectors of the another of the at least two focus/detector systems.

* * * * *